United States Patent [19]

McMullen

[11] 3,993,673

[45] Nov. 23, 1976

[54] PRODUCTION OF OLEFIN OXIDES

[75] Inventor: Charles Henry McMullen, Scarsdale, N.Y.

[73] Assignee: Union Carbide Corporation, New York, N.Y.

[22] Filed: Dec. 29, 1975

[21] Appl. No.: 645,038

Related U.S. Application Data

[63] Continuation-in-part of Ser. No. 553,583, Feb. 27, 1975, abandoned.

[30] Foreign Application Priority Data

Feb. 26, 1970 Germany .................................1942502
Sept. 27, 1973 Germany .................................2231374

[52] U.S. Cl. ......................................... 260/348.5 L
[51] Int. Cl.$^2$ ...................................... C07D 301/12
[58] Field of Search ............................. 260/348.5 L

[56] References Cited
UNITED STATES PATENTS

| | | | |
|---|---|---|---|
| 2,786,854 | 3/1957 | Smith et al. | 260/348.5 L |
| 2,833,787 | 5/1958 | Carlson et al. | 260/348.5 L |

FOREIGN PATENTS OR APPLICATIONS

| | | |
|---|---|---|
| 1,942,502 | 2/1970 | Germany |
| 2,231,374 | 9/1973 | Germany |

Primary Examiner—Norma S. Milestone
Attorney, Agent, or Firm—Bernard Lieberman

[57] ABSTRACT

A catalytic liquid phase process for the production of olefin oxides comprising admixing an olefin and hydrogen peroxide in the presence of an arsenic catalyst which is provided to the reaction as either elemental arsenic, an arsenic compound or mixtures thereof, the arsenic content of said compound being present in catalytically active amounts, said compound being essentially free of tungsten, molybdenum, vanadium and chromium; and the temperature of the admixture is in the range of about 25° to about 200° C.

15 Claims, No Drawings

PRODUCTION OF OLEFIN OXIDES

BACKGROUND OF THE INVENTION

This application is a continuation-in-part of my copending application Ser. No. 553,583, filed Feb. 27, 1975 and now abandoned.

This invention relates to a process for the production of olefin oxides and, more particularly, to a catalytic liquid phase process for the production of olefin oxides by the transfer of oxygen from hydrogen peroxide to an olefin substrate.

Olefin oxides are of considerable importance in the chemical industry as intermediates in the preparation of urethanes, glycol solvents, coating compositions, molded articles, surfactants, plasticizers and many other products. Consequently, for many years, producers of olefin oxides have been seeking process routes wherein the reactants are favored with high selectivity, high efficiency, and commercially acceptable reaction rates and there is a minimal by-product production. In the case of catalytic reactions it is preferred that intermediary epoxidizing species are avoided and that the catalysts are relatively easy and inexpensive to produce.

Various catalytic processes have been suggested to meet industrial needs such as olefin reactions with hydrogen peroxide in the presence of heteropolytungstic acids of arsenic, antimony or bismuth or the acid salts of heavy metal peracids; with molecular oxygen in the presence of arsenic catalysts; and with organic hydroperoxides in the presence of catalyst compounds or mixtures of compounds wherein at least one element from groups 4$b$ to 6$b$ and at least one element groups 4$a$ to 6$a$ of the Periodic Chart of the Elements are present (the Periodic Chart referred to herein is the one appearing in Lange's Handbook of Chemistry, Revised Tenth Edition). It was found, however, that none of these routes to olefin oxides met commercial needs, the organic hydroperoxide route producing large amounts of by-product and the other catalytic routes mentioned either significantly promoting ring-opening of the epoxide or other rearrangements, the production of intermediate peroxy compounds, and/or necessitating the use of expensive catalysts as well as lacking optimum selectivities, efficiencies, or reaction rates.

SUMMARY OF THE INVENTION

An object of the invention, therefore, is to provide a new process for the epoxidation of olefins which avoids the deficiencies heretofore mentioned and can be particularly counted on for high selectivity as well as high efficiency.

Other objects and advantages will become apparent hereinafter.

According to the present invention, a high efficiency and high selectivity catalytic liquid phase process for the production of olefin oxides has been discovered which comprises admixing an olefin and hydrogen peroxide in the presence of an arsenic catalyst which is provided to the reaction as either elemental arsenic, an arsenic compound or mixtures thereof, the arsenic content of said compound being present in catalytically active amounts, said compound being essentially free of tungsten, molybdenum, vanadium and chromium; and the temperature of the admixture is in the range of about 25° to about 200° C.

Those skilled in the art will appreciate that arsenic is generally grouped with the non-metals in the Periodic Chart of the Elements. See, for example, Lange's Handbook of Chemistry, Revised Tenth Edition.

DESCRIPTION OF THE PREFERRED EMBODIMENT

The process can be carried out by feeding a mixture of olefin and hydrogen peroxide into a reaction vessel. A liquid phase must be established and, depending on the nature of the olefin, pressure or a solvent may be necessary. The reaction vessel can be glass, glass-lined or made of aluminum or titanium. A glass-lined polytetrafluoroethylene coated stainless steel autoclave is found to be advantageous and unlined stainless steel can also be used effectively. A tubular reactor made of similar materials can also be used together with multi-point injection to maintain a particular ratio of reactants.

Some form of agitation is preferred to avoid a static system and can be accomplished by using a mechanically stirred autoclave, a multi-point injection system, or a loop reactor wherein the reactants are force circulated through the system. Sparging can also be used. It should be pointed out that agitation is inherent in continuous processes, but is enhanced by the use of the suggested modes of operation. In subject process, it is found that increased rates of reaction are obtained by good gas-liquid contact throughout and that this contact is provided by agitation. The homogeneity of the reactants, provided by the agitation, is also advantageous.

The olfin can be broadly defined as an epoxidizable olefinically unsaturated hydrocarbon compound. Thus, the olefin can include terminal olefins such as mono-functional and difunctional olefins having the following structural formulas, respectively:

wherein $R^1$ and $R^2$ can each be hydrogen or an alkyl radical, straight or branched chain, having 1 to 20 carbon atoms; and

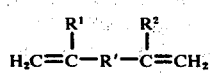

wherein $R^1$ and $R^2$ can each be hydrogen or an alkyl radical having 1 to 10 carbon atoms and $R'$ is from 0 to 10 methylene groups. The broad definition can also include cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins can be represented by the following structural formula:

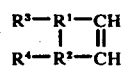

wherein $R^1$ and $R^2$ each can be alkylene radicals having 1 to 4 carbon atoms and $R^3$ and $R^4$ each represent hydrogen atoms or alkyl radicals, straight or branched chain, having 1 to 10 carbon atoms. The internal olefins can be represented by the following structural formula:

$$R^1R^2C=CR^3R^4$$

wherein $R^1$ and $R^3$ each are straight chain or branched chain alkyl radicals having 1 to 10 carbons atoms and $R^2$ and $R^4$ each can be hydrogen atoms or the same as $R^1$ and $R^3$. The broad definition can further include olefins derived from aromatic compounds, such as styrene and stilbene which can be represented by the following structural formulas:

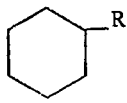 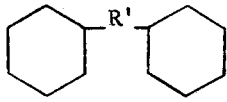

wherein R is a monovalent alkenyl radical having 2 to 10 carbon atoms and R' is a bivalent alkenyl radical having 2 to 5 carbon atoms.

Representative olefins are ethylene, propylene, butene-1, butene-2, isobutylene, pentene-1, hexene-1, pentene-2, octene-1, cyclopentene, cyclohexene, cyclooctene, 2-methylbutene-1, 3-methylbutene-1, heptene-1, hexene-2, hexene-3, octene-2, heptene-3, pentadecene-1, octadecene-1, dodecene-2, 2-methylpentene-2, tetramethylethylene, methylethylethylene, cyclobutene, cycloheptene, 2-methylheptene-1, 2,4,4,-trimethylpentene-1, 2-methylbutene-2, 4-methylpentene-2, and 2-ethyl, 3-methylbutene-1.

Heteroatom-containing olefins such as allyl alcohol and allyl chloride and other substituted olefins can also be used in subject process provided that the substituents are inert to hydrogen peroxide under the prescribed reaction conditions. Hydroxyl, halogen, and ether substituents can be used here as well as, e.g., RCOO—, —Si(OR)$_3$, —COOR, and aromatic substituents such as phenyl, etc. Additional examples of olefins are soya oil, linseed oil, 4-vinyl cyclohexene, butadiene, and polycyclic olefins such as norbornene.

The hydrogen peroxide can be used in aqueous solutions ranging from about 20 percent or 30 percent by weight hydrogen peroxide on up to anhydrous hydrogen peroxide which can, of course, also be used. It is preferred to use less water rather than more. Solutions of hydrogen peroxide in the solvents referred to below, formed either by addition to the solvent or by reaction to provide both hydrogen peroxide and solvent, are useful for incorporating the hydrogen peroxide in the process.

The catalyst may be provided to the reaction as elemental arsenic or an arsenic compound essentially free of tungsten, molybdenum, vanadium and chromium, or mixtures thereof. The term "mixtures" includes mixtures of elemental arsenic with one or more of the above-described arsenic compounds as well as mixtures of two or more of such arsenic compounds.

The catalyst can be used in homogeneous or heterogeneous systems; however, in the latter case the system should be adapted to provide sufficient contact between the reactants and the catalyst. Although this is accomplished by conventional techniques, the stirred reactor use in the homogeneous system is simpler and more economical.

The invention also contemplates the use of arsenic catalyst in conjunction with compounds having no catalytic effect on the olefin epoxidation reaction. For example, the arsenic catalyst may be combined with an additive intended to stabilize hydrogen peroxide in the reaction medium, e.g. zinc octanoate.

The arsenic can be provided to the reaction in any of its commonly available forms, such as elemental arsenic wherein the oxidation state is zero, arsenic trioxide where arsenic is present in the plus three state, or arsenic pentoxide where the oxidation state is plus five. It is recognized that arsenic in any of the above-described forms may be converted under reaction conditions to a catalytically active species.

Generally, the inorganic derivative contains at least one arsenic-to-oxygen bond or is converted to a species containing such a bond under reaction conditions. Illustrative of inorganic derivatives of arsenic are arsenic oxides, oxyacids of arsenic, salts and esters of the oxyacids of arsenic, arsenic halides, arsenic oxyhalides, and arsenic sulfides. The ester of the oxyacids of arsenic can be considered to be a combination of inorganic and organic derivatives.

The organic derivatives generally contain at least one carbon-to-arsenic bond.

Illustrative of organic derivatives, i.e. organometallic compounds, containing arsenic in the plus three oxidation state are those of the general formula RAsXY wherein R is an alkyl, aralkyl, or aryl radical and X or Y is hydrogen, alkyl, aralkyl, aryl, halogen, hydroxyl, alkoxy (—OR'), acyloxy (—OCOR'), —AsR'R", —OAsR'R", a nitrogen containing group, e.g., —NR'R", a phosphorus containing group, e.g., —PO(OR')$_2$ a silicon containing group, e.g., OSiR'$_3$, or a sulfur containing group. Compounds such as the arsenoso compounds, (RAsO)n, primary arsine oxides, RAsO, or heterocyclic derivatives of arsenic such as the arsolanes, AsR or arseno derivatives, (RAs=)n, can also be used. R', R", and R'" can be alkyl, aralkyl, or aryl groups and n is an integer representing the number of recurring units in the polymeric structure.

Compounds containing arsenic in the plus five oxidation state are exemplified by the general formula R'R"R'"AsXY where R', R", and R'" are as defined above and X or Y is alkyl, aralkyl, aryl, halogen, hydroxyl, alkoxy, —NO$_3$, or —SO$_4$H. Other useful classes of compounds have the general formulae R'R"As (=O)X and R'"As(=O)XY with R', R" and R'" as defined above, and X and Y as defined above in this paragraph.

Specific examples of the above derivatives are as follows:

| Name | Formula |
|---|---|
| Arsenic trioxide (Arsenolite) | As$_2$O$_3$ |
| Arsenic pentoxide | As$_2$O$_5$ |
| Arsenious acid | As(OH)$_3$ |
| Arsenic acid | H$_3$AsO$_4$ |
| Arsenic triethoxide | As(OC$_2$H$_5$)$_3$ |
| Arsenic triphenoxide | As(OC$_6$H$_5$)$_3$ |

-continued

| Name | Formula |
|---|---|
| 2,2'-ethylenedioxybis(1,3,2-dioxarsolane) | $\left[\begin{array}{c}O\\ \\O\end{array}\right\rangle As-O(CH_2)_2O-As\left\langle\begin{array}{c}O\\ \\O\end{array}\right]$ |
| 2,2'-oxydi-1,3,2-dioxarsolane | $\left[\begin{array}{c}O\\ \\O\end{array}\right\rangle As-O-As\left\langle\begin{array}{c}O\\ \\O\end{array}\right]$ |
| 1,4,6,9-tetraoxa-5-arsaspiro[4.4]- nonan-5-ol | $\begin{array}{c}O\\ \\O\end{array}\rangle\underset{\underset{OH}{\mid}}{As}\langle\begin{array}{c}O\\ \\O\end{array}$ |
| Arsenic trichloride | $AsCl_3$ |
| Arsenic oxychloride | $AsOCl$ |
| Arsenic trisulphide | $As_2S_3$ |
| Triphenylarsine | $(C_6H_5)_3As$ |
| Triphenylarsine oxide | $(C_6H_5)_3AsO$ |
| Hydroxybis(trifluoromethyl) arsine | $(CF_3)_2AsOH$ |
| Oxybis(dimethylarsine) | $[(CH_3)_2As]_2O$ |
| Phenoxydimethylarsine | $(CH_3)_2AsOC_6H_5$ |
| Benzenearsonous acid | $C_6H_5As(OH)_2$ |
| Bis(oxoarsino) methane | $CH_2(AsO)_2$ |
| Sodium arsenite | $NaAsO_2$ |
| Sodium arsenate | $Na_3AsO_4$ |
| Pharmacolite | $CaHAsO_4 . 2 H_2O$ |
| Aluminum arsenate | $AlAsO_4$ |
| Ammonium magnesium arsenate | $MgNH_4AsO_4 6 H_2O$ |
| Adamite | $Zn(ZnOH)AsO_4$ |
| Bismuth arsenate | $BiAsO_4 . 1/2 H_2O$ |
| Bismuth uranyl arsenate (Walpurgite) | $5Bi_2O_3 . 3 UO_3 . 2 As_2O_5 . 12 H_2O$ |
| Zirconium arsenate | $Zr_3As_4O_{16} 5 H_2O$ |
| Thallic arsenate | $TlAsO_4 . 2 H_2O$ |
| Thiobis(dimethylarsine) | $[(CH_3)_2As]_2S$ |
| Dimethyl(dimethylarsino) phosphonate | $(CH_3)_2AsPO(OCH_3)_2$ |
| Dichlorotris(trifluoromethyl)-arsenic | $(CF_3)_3AsCl_2$ |
| Methylphenylarsinic acid | $CH_3(C_6H_5)As\begin{array}{c}\\\diagup\!\!\!\diagup O\\\diagdown OH\end{array}$ |
| Poly(methylenearsinic acid) | $\left[\begin{array}{c}O\\ \|\|\\-CH_2As-\\ \|\\OH\end{array}\right]_n$ |
| Bis(4-nitrophenyl) arsinic acid | $(4-O_2NC_6H_4)_2As\begin{array}{c}\\\diagup\!\!\!\diagup O\\\diagdown OH\end{array}$ |
| Phenoxarsinic acid | (phenoxarsine ring with =O and OH on As) |
| Butanearsonic acid | $C_4H_9AsO_3H_2$ |
| 4-Bromobenzenearsonic acid | $4-BrC_6H_4AsO_3H_2$ |
| 1-Phenylarsolane | (arsolane ring with As–$C_6H_5$) |

As noted, mixtures of any of the aforementioned catalysts can be used.

Where supported heterogeneous catalysts are desired, they can be loaded onto a support by any of the known conventional techniques such as impregnation, precipitation, etc. The support can be a naturally occurring material, e.g., a clay or aluminosilicate, or a synthetic material such as zeolite, silica gel, or alumina having a surface area in the range of about one square meter per gram to about 800 square meters per gram. The catalyst can also be attached to a polymeric backbone such as a polysilane, again, by conventional methods.

The arsenic catalyst can be soluble, partially soluble, or insoluble. Of course, contact of the reactants with the catalyst is essential, and different conventional techniques are used to provide this contact.

The reaction medium must be one in which the olefin and the hydrogen peroxide solution are soluble under reaction conditions, i.e., it must be capable of maintaining a liquid phase throughout the reaction. It should also be inert to the reactants and the catalyst. Generally, a conventional inert organic solvent is used as the reaction medium. A very wide choice is permitted which includes ethers, esters, alcohols, glycols, other oxygenated solvents, chlorinated solvents including chlorinated hydrocarbons and chlorinated aromatics, and sulfolane. Where gaseous olefins are used, it is desirable that a solvent be selected that will increase the solubility of the olefin. A representative list of solvents appears in examples 31 to 41. Other useful solvents are ethyl acetate, tetraethylene glycol, dimethylformamide, nitromethane, tetrahydrofuran, acetone, phenyl acetate, diphenyl CARBITOL, propylene glycol diacetate, cyclohexylacetate, triethyl phosphate, and 2,2-dimethoxypropane. Co-solvents such as toluene, benzene, chlorobenzene, ortho-dichlorobenzene, nitrobenzene, 1,1,2,2-tetrachloroethane, n-pentane, cyclohexane, and anisole can also be used. Mixture of solvents as well as co-solvents can also be used. There is an exception to the use of a solvent inert to the reactants and that is where a liquid olefin reactant is used to provide the liquid phase.

The reaction can be conducted in an atmosphere of air or oxygen since the olefin selectively reacts with the hydrogen peroxide in preference to the molecular oxygen; however, the reaction is preferably conducted in an essentially oxygen-free atmosphere. This is provided by conventional means, e.g., by using an inert gas such as nitrogen, argon, or helium as the atmosphere in which the process is carried out.

The pressure is generally in the range of about atmospheric pressure to about 1500 psia. Pressure is selected according to the olefin used since it will define the concentration of gaseous olefin which can be maintained in the liquid phase at reaction temperature.

The temperature of the reaction can be in the range of about 25° to about 200° C. and is preferably in the range of about 60° to about 130° C. Lower temperatures than 25° C. can be used if reaction rates are sacrificed.

The time of the reaction is simply that in which one or the other reactants, usually the hydrogen peroxide, is used up. This is applicable in batch and semi-continuous processes to which subject process can be applied. In continuous processes, which are preferred for commercial use, the reactants are continuously fed so that time of reaction is merely the measure of the length of each cycle.

A molar ratio of about 0.5 moles to about 200 moles of olefin per mole of hydrogen peroxide can be used; however, a molar excess of olefin is suggested. The preferred molar ratio is in the range of about 2 moles to about 20 moles of olefin per mol of hydrogen peroxide.

As noted, a catalytically active amount of catalyst is required. There is really no upper limit except the bounds of economy. Generally, a molar ratio of about 0.0001 gram atom to about 1 gram atom of arsenic per mole of hydrogen peroxide is satisfactory while a molar ratio of about 0.001 gram atom to about 0.1 gram atom of arsenic per mole of hydrogen peroxide is preferred.

The ratios of olefin and hydrogen peroxide can be kept fairly constant by the use of a continuous process and by analyzing the outlet ratio and adjusting the feed ratio. In a backmixed reactor, the feed is adjusted until the outlet ratio is within the prescribed range. Where two or more reactors are used in series or the reactor is tubular with multi-point injection, the reactions taking place are considered to be a series of batch reactions and are carefully monitored to insure for the most part that the molar ratio in any one reaction is not permitted to go below or rise above a desired range.

The amount of reaction medium or solvent is determined by the amount needed to maintain the liquid phase. Generally, the amount is in the range of about 5 percent by volume to about 95 percent by volume based on the volume of the total reaction mixture including olefin, hydrogen peroxide solution, catalyst and solvent. It is preferably in the range of about 25 percent by volume to about 75 percent by volume. Other quantities of solvent can be used, however, so long as there is a sufficient amount to maintain the reaction in the liquid phase.

One of the features of this invention is that the solvent is not degraded during the reaction as in the case where molecular oxygen is used to epoxidize olefins in the presence of arsenic catalysts.

Recovery, separation and analysis of products and unreacted materials are accomplished by conventional means.

The reaction is found to be clean, i.e, having minimal by-product formation. Olefin efficiencies approach 100 percent and hydrogen peroxide efficiencies approach 80 to 95 percent.

The following examples illustrate the invention. Percentages are by weight unless otherwise specified. Moles and percentages of hydrogen peroxide are calculated on an anhydrous basis and those of catalyst are calculated for arsenic.

EXAMPLES 1 TO 14

The olefin is reacted with a 95 percent aqueous solution of hydrogen peroxide (95% $H_2O_2$ + 5% water) in the presence of an arsenic trioxide catalyst in 1,4-dioxane solvent. The olefin, hydrogen peroxide solution, catalyst, and solvent are mixed together in a 100 milliliter Pyrex flask at room temperature under one atmosphere of argon. The reaction mixture is then heated to 90° C. Samples are withdrawn periodically and analyzed for residual peroxide by the iodometric method and for epoxide by gas-chromatography or by titration using the tetramethylammonium bromide-perchloric acid method.

Variable conditions and results are set forth in Table I.

Table I

| Ex. | Olefin | Olefin (millimoles) | $H_2O_2$ (millimoles) | $As_2O_3$ (millimoles) | 1,4-dioxane (milliliters) | Reaction Time (Hours) | Epoxide (millimoles) | $H_2O_2$ Converted (mole %) |
|---|---|---|---|---|---|---|---|---|
| 1 | Octene-1 | 330 | 54 | 0.54 | 44 | 5 | 40 | 88 |
| 2 | Styrene | 165 | 27 | 0.27 | 29 | 4 | 24 | 95 |
| 3 | 2-Octene[1] | 165 | 27 | 0.27 | 22 | 6 | 24 | 94 |
| 4 | cis-2-Octene | 67 | 11 | 0.11 | 8 | 2 | 10 | 95 |
| 5 | trans-2-Octene | 67 | 11 | 0.11 | 8 | 3 | 9 | 89 |
| 6 | Cyclohexene[2] | 82 | 27 | 0.53 | 80 | 5 | 17 | 80 |
| 7 | Allylpentyl ether | 82 | 13 | 0.13 | 10 | 2 | 1 | 58 |
| 8 | Allyl alcohol | 165 | 27 | 0.27 | 36 | 1 | 3 | 30 |
| 9 | Soya oil | 22[3] | 27 | 0.27 | 24 | 4 | 25 | 100 |

Table I-continued

| Ex. | Olefin | Olefin (millimoles) | $H_2O_2$ (millimoles) | $As_2O_3$ (millimoles) | 1,4-dioxane (milliliters) | Reaction Time (Hours) | Epoxide (millimoles) | $H_2O_2$ Converted (mole %) |
|---|---|---|---|---|---|---|---|---|
| 10 | Linseed oil | 22[3] | 27 | 0.27 | 24 | 3 | 25 | 100 |
| 11 | 2-Ethylhexyltallate | 22[3] | 27 | 0.27 | 24 | 3 | 23 | 94 |
| 12 | Vinyltriethoxysilane | 165 | 27 | 0.27 | 14 | 3.5 | 10 | 98 |
| 13 | Allyltrimethoxysilane | 165 | 27 | 0.27 | 22 | 1.5 | 20 | 100 |
| 14 | 4-Vinyl cyclohexane | 165 | 27 | 0.27 | 21 | 1 | 23 | 89 |

[1]85:15 cis-trans mixture
[2]reaction temperature 70° C
[3]Weight in grams

EXAMPLE 15

$2.0 \times 10^{-3}$ mole of arsenic trioxide, 300 ml. of 1,4-dioxane solvent, 15 ml. of n-nonane internal standard, $4.1 \times 10^{-1}$ mole of hydrogen peroxide (95 percent aqueous solution) and 3.1 moles of propylene are charged to a one-liter, 316 stainless-steel, stirred autoclave, at room temperature. The reactor is pressurized with 200 psig of argon and is then heated to 90° C. Samples of the liquid-phase are withdrawn at intervals and analyzed for residual peroxide by the iodometric method and for epoxide by gas chromatography. After 6 hours, $2.7 \times 10^{-1}$ moles of propylene oxide are produced and 79 mole percent of the initial peroxide is consumed.

EXAMPLE 16

Example 15 is repeated except that 2.5 moles of isobutylene are substituted for propylene. After 6 hours, at 90° C, $3.2 \times 10^{-1}$ mole of epoxide is produced and 95 mole percent of the peroxide is consumed.

EXAMPLE 17

Example 15 is repeated except that 3.2 moles of ethylene are substituted for propylene and $4.0 \times 10^{-3}$ mole of arsenic trioxide catalyst is used. After 3 hours, at 90° C, 40 mole percent of the initial peroxide is consumed and ethylene oxide is the major product detected.

EXAMPLE 18

$2.7 \times 10^{-4}$ mole of arsenic triethoxide catalyst dissolved in 1.1 ml. of 1,4-dioxane, 2.0 ml. of n-undecane internal standard, $1.65 \times 10^{-1}$ mole of allyl chloride, 32.9 ml. of 1,4-dioxane, and $2.7 \times 10^{-2}$ moles of a 97 percent aqueous solution of hydrogen peroxide (97% $H_2O_2$ + 3% $H_2O$) are mixed together in a 100 milliliter flask at room temperature. A 2.0 ml. aliquot of this mixture is frozen, evacuated and sealed under vacuum in a thick-wall Pyrex glass tube (pressure = autogenous) and the immersed in an oil bath at 90° C. After 8 hours the tube is removed from the bath and analysis of the contents shows that 72 mole percent of the peroxide is consumed and the yield of epichlorohydrin is 50 mole percent.

EXAMPLE 19

$5.0 \times 10^{-4}$ mole of arsenic trioxide catalyst, $8.0 \times 10^{-2}$ mole of cyclohexene, 80 ml. of 1,4-dioxane and 2.5 ml. of 28 percent aqueous hydrogen peroxide solution (28% $H_2O_2$ + 72% $H_2O$) are mixed at room temperature in a 100 milliliter flask (under argon at atmospheric pressure) which is then immersed in a bath at 90° C. After 35 minutes of reaction, cycohexene oxide is detected in the mixture.

Examples 20 to 30

Octene-1 (3.3 moles) is reacted with 95 percent aqueous solution of hydrogen peroxide ($5.4 \times 10^{-1}$ mole of $H_2O_2$) in the presence of various arsenic catalysts ($5.4 \times 10^{-3}$ mole arsenic compound) in 1,4-dioxane solvent (45 volume percent based on the method of the reaction mixture) at 90° C. by the method described for example 1. The epoxide efficiency is defined as:

$$\frac{\text{moles of epoxide produced}}{\text{moles of peroxide consumed}} \times 100\%$$

Variable conditions and results are set forth in Table II.

Table II

| Example | Catalyst | Reaction Time (hours) | Epoxide Efficiency (%) | $H_2O_2$ Conversion (mole %) |
|---|---|---|---|---|
| 20 | Arsenic triethoxide | 4 | 96 | 76 |
| 21 | 2,2'-Ethylenedioxybis-(1,3,2-dioxarsolane) | 5 | 98 | 74 |
| 22 | Elemental Arsenic | 4 | 80 | 84 |
| 23 | Phenyl arsine oxide | 4 | 90 | 64 |
| 24 | Arsenic pentoxide | 6 | 86 | 76 |
| 25 | Arsenic acid | 3 | 73 | 66 |
| 26 | Arsenic trichloride | 4 | 82 | 75 |
| 27 | Benzene arsonic acid | 4 | 70 | 67 |
| 28 | n-Propyl arsonic acid | 19 | 37 | 83 |
| 29 | Triphenylarsine | 23 | 42 | 17 |
| 30 | Triphenylarsine oxide | 23 | 38 | 19 |

EXAMPLES 31 TO 41

Octene-1 (3.3 moles) is reacted with a 95 percent aqueous solution of hydrogen peroxide ($5.4 \times 10^{-1}$ mole of $H_2O_2$) in the presence of arsenic trioxide catalyst ($5.4 \times 10^{-3}$ mole) in various solvents, each in an amount of 45 volume percent based on the total volume of the reaction mixture. For the solvents boiling below 90° C, the method described in example 18 is used, and for the solvents boiling above 90° C, the method described in example 1 is used. Variable conditions and results are set forth in Table III.

Table III

| Example | Solvent | Reaction Time Hrs. | Epoxide Efficiency (%) | $H_2O_2$ Conversion (mole %) |
|---------|---------|--------------------|-----------------------:|------------------------------:|
| 31 | Ethanol | 1 | 82 | 16 |
| 32 | 2-Propanol | 2 | 66 | 12 |
| 33 | t-Butanol | 2 | 74 | 8 |
| 34 | Methyl CELLOSOLVE | 1 | 96 | 19 |
| 35 | 1,2-Dimethoxy ethane | 1 | 78 | 44 |
| 36 | Diethyl CARBITOL | 1 | 75 | 66 |
| 37 | 1,4-Dioxane (35 vol. %) Chloroform (10 vol. %) | 1 | 84 | 38 |
| 38 | Methyl acetate | 1 | 83 | 48 |
| 39 | Methyl CELLOSOLVE acetate | 1 | 90 | 70 |
| 40 | Glycol diacetate | 1 | 92 | 69 |
| 41 | Diethylene glycol diacetate | 5 | 96 | 95 |

EXAMPLE 42

Cyclohexene ($8.2\times10^{-2}$ moles) is reacted with 93 percent aqueous hydrogen peroxide ($2.1\times10^{-2}$ moles of $H_2O_2$) in the presence of sodium arsenite catalyst ($1.0\times10^{-4}$ moles) in 80 ml. of 1,4-dioxane solvent at 70° C by the method described for example 19. The catalyst is substantially insoluble in the reaction mixture. After 30 minutes of reaction, cyclohexene oxide is detected in the mixture.

EXAMPLE 43

Octene-1 ($1.7\times10^{-1}$ moles) is reacted with 95 per cent aqueous hydrogen peroxide, ($2.7\times10^{-2}$ moles of $H_2O_2$) in 1,4-dioxane solvent, (45 volume percent), at 90° C, in the presence of arsenic trioxide ($2.7\times10^{-4}$ moles) and zinc octanoate ($1.1\times10^4$ moles), by the method described for example 1. After 2 hours 6 percent of the octene-1 is converted to epoxide.

EXAMPLE 44

Example 43 is repeated except that magnesium acetylacetonate ($5.4\times10^{-4}$ moles) is used in conjunction with arsenic trioxide catalyst ($2.7\times10^{-4}$ moles). After 3 hours, at 90° C, 1 percent of the octene-1 is converted to epoxide.

What is claimed is:

1. A catalytic liquid phase process for the production of olefin oxides comprising admixing an olefin and hydrogen peroxide in the presence of an arsenic catalyst which is provided to the reaction as either elemental arsenic, an arsenic compound or mixtures thereof, the arsenic content of said compound being present in catalytically active amounts, said compound being essentially free of tungsten, molybdenum, vanadium and chromium; and the temperature of the admixture being in the range of about 25° to about 200° C.

2. The process defined in claim 1 wherein the molar ratio of olefin to hydrogen peroxide is about 0.5 mole to about 200 moles of olefin per mole of hydrogen peroxide.

3. The process defined in claim 2 wherein the molar ratio of arsenic to hydrogen peroxide is about 0.0001 gram atom to about 1 gram atom of arsenic per mole of hydrogen peroxide.

4. The process defined in claim 3 wherein the process is conducted in an inert organic solvent.

5. The process defined in claim 4 wherein the temperature is in the range of about 60° to about 130° C.

6. The process defined in claim 5 wherein the molar ratio of arsenic to hydrogen peroxide is about 0.001 gram atom to about 0.1 gram atom per mole of hydrogen peroxide.

7. The process defined in claim 6 wherein the olefin is propylene.

8. The process defined in claim 7 wherein there is a molar excess of olefin over hydrogen peroxide.

9. The process defined in claim 8 wherein the molar ratio of olefin to hydrogen peroxide is about 2 moles of olefin per mole of hydrogen peroxide.

10. The process defined in claim 1 wherein the hydrogen peroxide is present in the form of an aqueous solution containing at least about 20 percent by weight hydrogen peroxide based on the weight of the aqueous solution.

11. The process defined in claim 1 wherein the process is conducted in an essentially oxygen-free atmosphere.

12. The process defined in claim 4 wherein the hydrogen peroxide is present in the form of an aqueous solution containing at least about 20 percent by weight hydrogen peroxide based on the weight of the aqueous solution.

13. The process defined in claim 9 wherein the hydrogen peroxide is present in the form of a aqueous solution containing at least about 20 percent by weight hydrogen peroxide based on the weight of the aqueous solution.

14. The process defined in claim 3 wherein the process is conducted in an essentially oxygen-free atmosphere.

15. The process defined in claim 13 wherein the process is conducted in an essentially oxygen-free atmosphere.

* * * * *